(12) United States Patent
Song et al.

(10) Patent No.: US 7,796,843 B2
(45) Date of Patent: Sep. 14, 2010

(54) DESIGN AND PERFORMANCE OF A FIBER BRAGG GRATING DISPLACEMENT SENSOR FOR MEASUREMENT OF MOVEMENT

(75) Inventors: Gangbing Song, Pearland, TX (US); Philip C. Noble, Houston, TX (US); Liang Ren, Dalian (CN); Michael Conditt, Houston, TX (US)

(73) Assignee: University of Houston, Houston, TX (US)

( * ) Notice: Subject to any disclaimer, the term of this patent is extended or adjusted under 35 U.S.C. 154(b) by 0 days.

(21) Appl. No.: 12/052,170

(22) Filed: Mar. 20, 2008

(65) Prior Publication Data
US 2009/0022450 A1 Jan. 22, 2009

Related U.S. Application Data

(60) Provisional application No. 60/896,200, filed on Mar. 21, 2007.

(51) Int. Cl.
*G02B 6/00* (2006.01)

(52) U.S. Cl. .......................... 385/12; 385/13
(58) Field of Classification Search .................. None
See application file for complete search history.

(56) References Cited

U.S. PATENT DOCUMENTS

| 2,788,422 | A | * | 4/1957 | Marbury | 337/18 |
|---|---|---|---|---|---|
| 5,599,668 | A | * | 2/1997 | Stimpson et al. | 435/6 |
| 6,471,710 | B1 | * | 10/2002 | Bucholtz | 606/130 |
| 6,802,838 | B2 | * | 10/2004 | Loeb et al. | 606/13 |
| 2002/0009252 | A1 | * | 1/2002 | Maron et al. | 385/12 |
| 2004/0057654 | A1 | * | 3/2004 | Baasch et al. | 385/16 |
| 2006/0247724 | A1 | * | 11/2006 | Gerber et al. | 607/41 |
| 2007/0156019 | A1 | * | 7/2007 | Larkin et al. | 600/104 |

* cited by examiner

*Primary Examiner*—Uyen-Chau N Le
*Assistant Examiner*—Chad H Smith
(74) *Attorney, Agent, or Firm*—Winstead PC

(57) ABSTRACT

A displacement sensor based on the underlying principle that when the outer surface of a quartz fiber (fiber optic cable) is etched to form a series of regularly spaced lines (a Fiber Bragg grating), laser light of a wavelength matching the spacing of the lines which enters one end of the fiber will be preferentially reflected. If the fiber is deformed, causing the line spacing to change, the wavelength of the reflected light will also change. This shift can be accurately measured and so can be related to the magnitude of the deformation of the fiber. This fiber is potted with epoxy resin in a narrow tube fabricated from a shape-memory alloy (SMA), and pre-formed into a curved shape. This not only protects the quartz fiber from direct contact with other objects and excessive bending, but also causes it to deform in a predictable fashion, thereby generating a reproducible response to displacement. Due to the high elastic behavior of the SMA tube, a displacement sensor with a gage length of 40 mm can measure displacements in excess of 3 mm.

11 Claims, 4 Drawing Sheets

Figure 1:
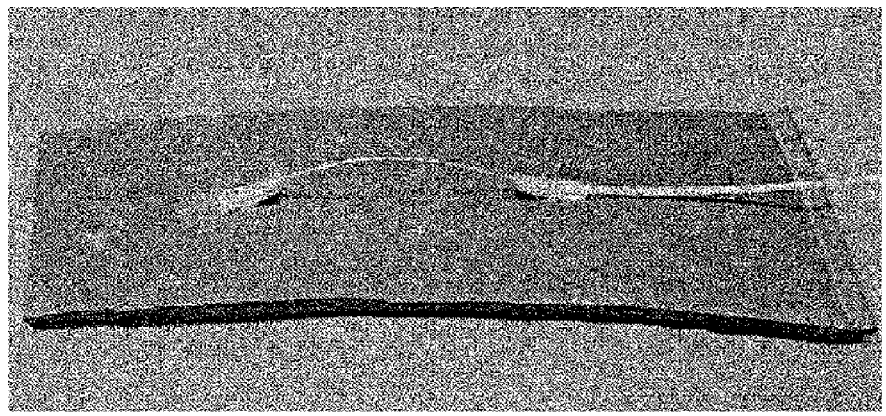

The schematic of an FBG displacement sensor

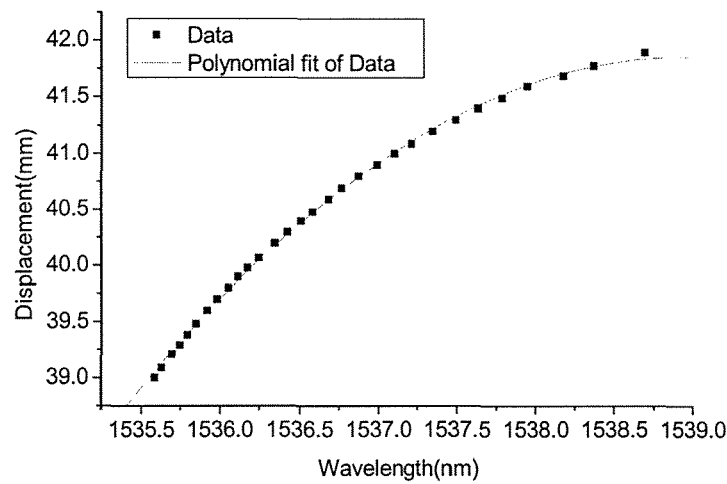
Fig.3 FBG displacement sensor calibration result
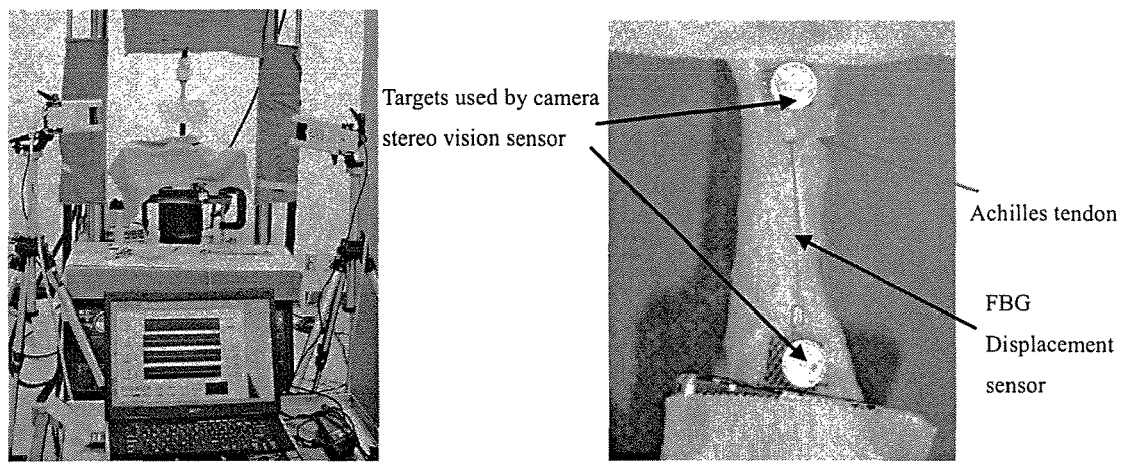
Figure 4. Depiction of testing device.

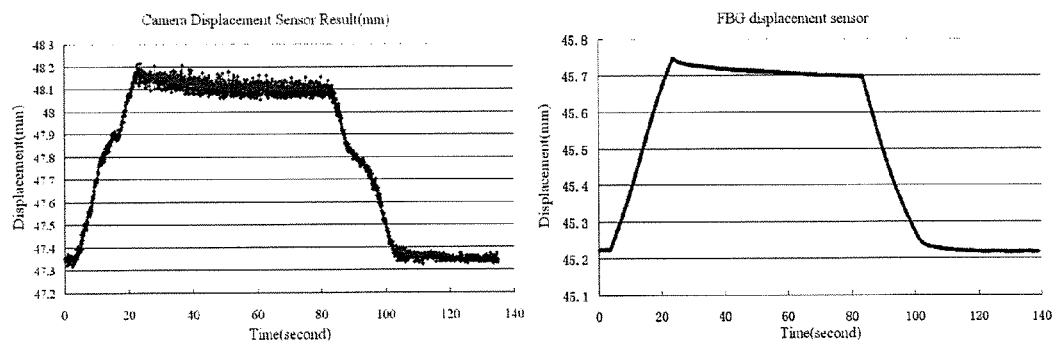
Figure 5. Comparison of Measured Tendon Elongation between FBG Sensor and Camera Stereo Vision Sensor
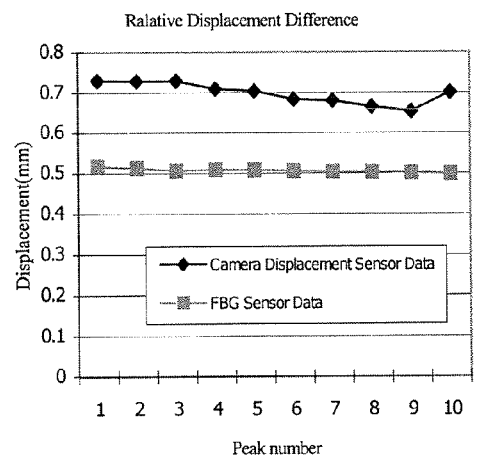
Figure 6. Repeatability and stability investigation of FBG sensor and camera stereo vision sensor.

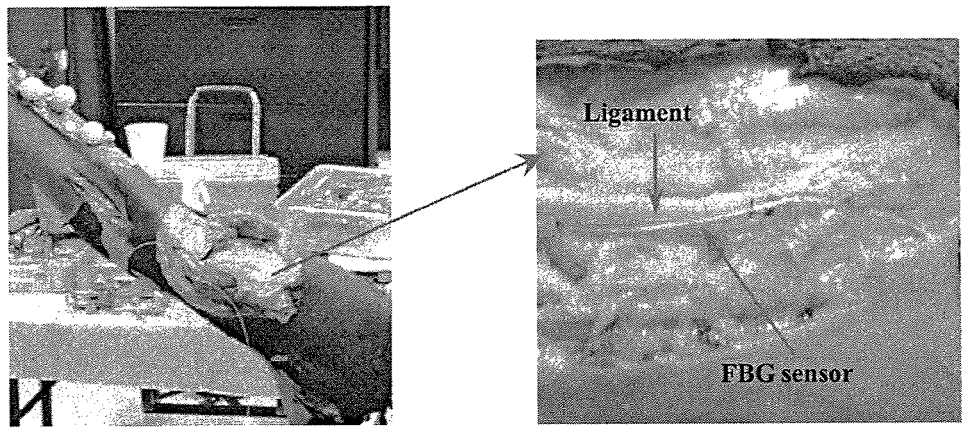
Fig. 7 The specimen with surface-mounted FBG sensors in the ligaments
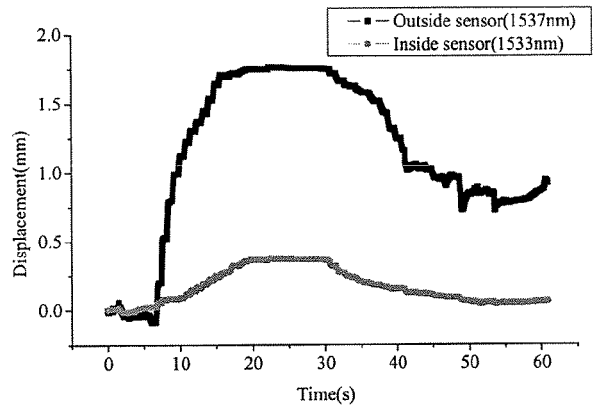
Figure 8: Results of FBG Sensors when Specimen was in Horizontal Position
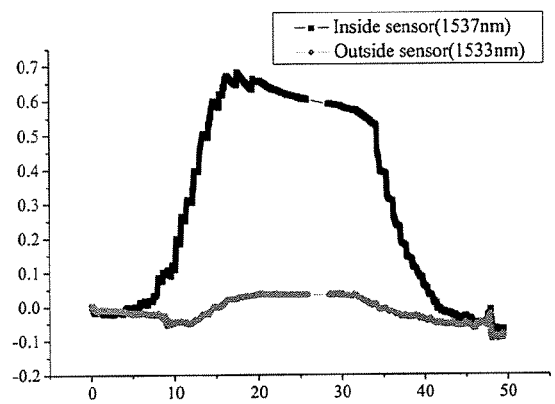
Figure 9: Results of FBG Sensors when the Specimen was in Vertical Position

DESIGN AND PERFORMANCE OF A FIBER BRAGG GRATING DISPLACEMENT SENSOR FOR MEASUREMENT OF MOVEMENT

CROSS-REFERENCE TO RELATED APPLICATION

This application claims priority to U.S. Provisional Patent Application No. 60/896,200, filed Mar. 21, 2007, the contents of which are incorporated herein by reference.

BACKGROUND OF THE INVENTION

1. Field of the Invention

The invention relates to measurement of movement using Fiber Bragg Grating.

2. Description of the Background Art

During normal loading, ligaments generally experience strains of one to two orders of magnitude larger than relatively stiff tissues, such as bone. Accordingly, measurements of changes in the length of ligaments under various dynamic conditions are useful indicators of soft-tissue loading. Current stereo-optic methods of measuring changes in ligament length provide three-dimensional measurements of tissue strains without the need for direct ligamentous contact. In many applications in research and industry, it is necessary to measure the deformation of mechanical structures during application of loads. Typically, this is achieved through the attachment of transducers to the loaded object. These transducers convert small changes in length between points of attachment to the underlying object to an electrical signal which can be recorded and converted to surface displacements. Another method is non-contacting and uses optical methods to record the relative position of markings drawn on the surface of deforming objects, or unique surface features. By tracking the spatial location of these markings, before and after loading, it is possible to determine the displacement that has occurred. While these methods are satisfactory for many applications, they have the following inherent limitations:

a) Excessive bulk for use in situations where space is limited;

b) Excessive weight for use with fragile or flexible substrates;

c) Expensive, especially optical systems;

d) Difficulties with reliable attachment to substrate surfaces;

e) Poor accuracy and/or repeatability;

f) Unacceptable noise and/or signal drift.

These weaknesses are particularly apparent in the testing of low-modulus and viscoelastic materials, especially biological tissues. In this application, coupling to tissues is often unreliable and leads to measurement artifacts. The present invention addresses each of the deficiencies listed with a sensor which is extremely light-weight, compact, accurate and repeatable. This invention can be used in any application where measurement of movement is desired.

DESCRIPTION OF FIGURES AND TABLES

FIG. 1. Schematic of an FBG displacement sensor.

Figure 2:
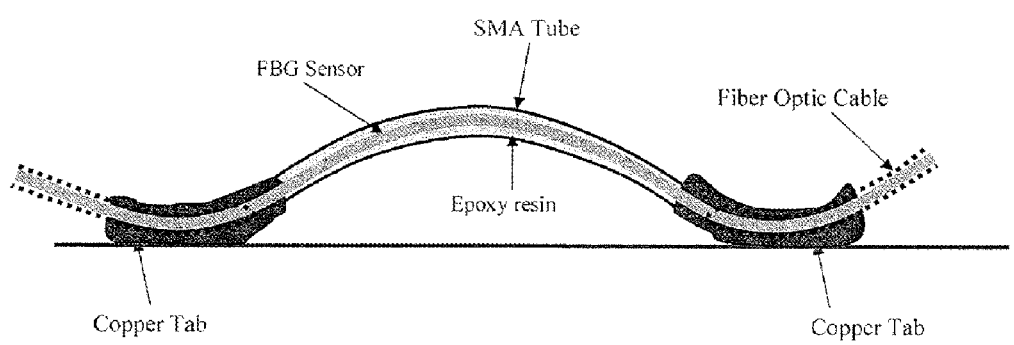

FIG. 2. Diagrammatic Representation of the FBG Displacement Sensor Mounted on a Surface.

FIG. 3. FBG displacement sensor calibration results.

FIG. 4. Depiction of testing device.

FIG. 5. Comparison of Measured Tendon Elongation between FBG Sensor and Camera Stereo Vision Sensor.

FIG. 6. Repeatability and stability investigation of FBG sensor and camera stereo vision sensor.

FIG. 7. The specimen with surface-mounted FBG sensors in the ligaments.

FIG. 8. Results of FBG Sensors when Specimen was in Horizontal Position.

FIG. 9. Results of FBG Sensors when the Specimen was in Vertical Position.

SUMMARY OF THE INVENTION

As illustrated in FIGS. 1-2, we have developed a displacement sensor based on the underlying principle that when the outer surface of a quartz fiber (fiber optic cable) is etched to form a series of regularly spaced lines (a Fiber Bragg grating), laser light of a wavelength matching the spacing of the lines which enters one end of the fiber will be preferentially reflected. If the fiber is deformed, causing the line spacing to change, the wavelength of the reflected light will also change. This shift can be accurately measured and so can be related to the magnitude of the deformation of the fiber. This fiber is potted with epoxy resin in a narrow tube fabricated from a shape-memory alloy (SMA), and pre-formed into a curved shape. This not only protects the quartz fiber from direct contact with other objects and excessive bending, but also causes it to deform in a predictable fashion, thereby generating a reproducible response to displacement. Due to the high elastic behavior of the SMA tube, a displacement sensor with a gage length of 40 mm can measure displacements in excess of 3 mm.

DETAILED DESCRIPTION OF THE INVENTION

We have developed a displacement sensor based on the underlying principle that when the outer surface of a quartz fiber (fiber optic cable) is etched to form a series of regularly spaced lines (a Fiber Bragg grating), laser light of a wavelength matching the spacing of the lines which enters one end of the fiber will be preferentially reflected. If the fiber is deformed, causing the line spacing to change, the wavelength of the reflected light will also change. This shift can be accurately measured and so can be related to the magnitude of the deformation of the fiber. In practice, quartz fibers are extremely brittle and break easily with use in measurement applications. Moreover, given their small diameter, and the gage length needed for most applications (3-10 mm), most fiber-based sensors would have a large length to diameter ratio. This causes the deformed shape of the fiber to vary with loading, leading to variable and unreliable output. To overcome these problems, the fiber is potted with epoxy resin in a narrow tube fabricated from a shape-memory alloy (SMA), and pre-formed into a curved shape. This not only protects the quartz fiber from direct contact with other objects and excessive bending, but also causes it to deform in a predictable fashion, thereby generating a reproducible response to displacement. Due to the high elastic behavior of the SMA tube, a displacement sensor with a gage length of 40 mm can measure displacements in excess of 3 mm.

3. Principle of Operation

As illustrated in FIG. 2, the SMA tube is attached to the surface of an object via two thin copper tabs which serve as supporting anchors. The anchors also serve to protect the fiber cable from damage from loads applied to the cable attached to the sensor. Another mode of use involves placing the sensor within a hole or other cavity within the surface of the object. The sensor may be held in place with adhesive or by embedding, or the hole or cavity may be undersized compared to the sensor such that the sensor must be partially straightened to allow its placement. Once the sensor is in position, displacement of the substrate causes a change in the distance between the attachment points of the tube to the substrate. This alters the curvature of the tube, inducing a strain variation on the FBG sensor. The strain change of the FBG can be detected by the shift in the Bragg wavelength according to the sensing principle. The Bragg element is post-tensioned to ensure that it is always loaded in tension.

4. Test Results

To characterize the performance of the FBG displacement sensor, the sensor was mounted on a vernier caliper in order to apply known values of displacement from 39.0 mm to 42.0 mm (FIG. 3). The calibration results show that the change in wavelength of the laser beam reflected by the fiber-optic grating of the FBG sensor varies nonlinearly with displacement of the device. The measured shift in Bragg wavelength is a binomial function of the applied displacement, with a correlation coefficient of greater than 0.999.

5. Experiments with Biologic Tissues 5.1 Achilles Tendon Tests

To verify the performance of the FBG displacement sensor, the elongation of an Achilles tendon specimen was monitored simultaneously with the FBG displacement sensor and a two-camera stereo vision sensor (PC Reflex, Qualysis, Sweden). The FBG displacement sensor and two targets used by the stereo vision sensors were mounted on the surface of a 10 cm section of a cadaveric Achilles tendon, as presented in FIG. 4. The construct was mounted in a materials testing device (Bionix, MTS Systems Corp.) (FIG. 4). The distance between the two targets used by camera stereo vision sensor was approximately 5 mm larger than the gage length of FBG displacement sensor.

The tendon was given a small preload (10 N) for a 3 second holding period, and then elongated at 0.1 mm/second for 20 seconds and held at 2 mm extension for 60 seconds. The specimen was then returned to the initial, unloaded condition at a constant rate of 0.1 mm/second. FIG. 5 shows the results of specimen tendon deformation monitored by the camera sensor and by the FBG sensor, respectively. It can be seen that both displacement curves are similar in shape. However, the noise of the displacement data generated by the stereo vision sensor is approximately ±0.055 mm, an order of magnitude larger than the output of the BG sensor, which is only ±0.006 mm. Compared to the stereo-optic measurement technique, it can be seen that the FBG sensor exhibits a special advantage of high sensitivity and a low signal to noise ratio without any loss of accuracy.

To assess the reproducibility of the fiberoptic sensor in measuring tissue strains, a series of 10 sets of loading-unloading cycles was then performed by displacing the specimen from 0 mm to 2 mm. The displacement peak values monitored by these two types of sensors are shown in FIG. 6. The results demonstrate that the behavior of FBG sensor was more steady and repeatable than the behavior of the camera stereo vision sensor. There exists a small difference between camera and FBG sensors due to the different gauge lengths of these two sensors. This is attributable to the increased gage length (5 mm) of the optical system compared to the FBG sensor. This experiment does not limit the use of this invention which can be used in any application where measurement of movement is desired.

5.2 Measuring Ligament Strains in the Knee

A common experimental problem in joint biomechanics is the monitoring of ligament strains during joint motion in cadaveric specimens. To evaluate the suitability of the fiber-optic sensors for this application, two FBG displacement sensors were mounted directly onto the medial and lateral collateral ligaments of a human cadaver after removal of the soft tissue encapsulating each structure. The supporting anchors of the FBG sensor were bonded to each ligament with cyanoacrylate adhesive (FIG. 7). In addition to the strain signal, the fiber grating is also sensitive to temperature. Temperature compensation in this experiment is implemented by integrating another FBG sensor in close proximity to the first.

To generate loads within each ligament, the joint surfaces were distracted by placing a hydraulic knee spreader between the femur and the tibia. Using this device, equal loads of approximately 40N were applied to both the medial and lateral compartments of the knee joint for approximately 15 seconds, after which time, the knee was returned to its original unloaded condition.

FIGS. 8 and 9 show the response of the FBG sensor to distraction of the joint with the extremity placed in horizontal and vertical orientations. The figures show that the deformation of the inside (medial) ligament is apparently larger than the outside (lateral) ligament and that joint loading in the horizontal posture leads to increased ligament strain.

We claim:

1. A displacement transducer comprising:
an optical fiber potted in epoxy, wherein said optical fiber has been etched with a grating; and
a tube fabricated from a shape memory alloy, wherein said optical fiber and said epoxy are substantially encased in said tube, and wherein said displacement transducer is mounted on a biological surface.

2. The displacement transducer of claim 1, wherein said transducer is mounted on a biological surface to measure a deformation of said surface.

3. A displacement sensor comprising:
a fiber optic cable etched with a series of regularly spaced lines to form a Fiber Bragg grating, wherein said fiber optic cable is potted in epoxy and substantially encased in a tube formed from a shape memory alloy, and wherein said displacement sensor is mounted on a biological surface;
a laser light source with a wavelength matching the line spacing of the regularly spaced lines wherein the laser light source is oriented to direct light into one end of the fiber optic cable to provide preferential reflection; and
apparatus for determining light wavelength changes and reporting fiber deformation as a function of change in the light wavelength.

4. The displacement sensor of claim 3, wherein said tube is pre-formed into a curved shape.

5. The displacement sensor of claim 3, wherein said tube is pre-formed into a curved shape.

6. The displacement transducer of claim 1, wherein said grating comprises a Fiber Bragg grating.

7. The displacement transducer of claim 1, wherein said transducer further comprises one or more supporting anchors for the transducer on to a surface.

8. The displacement transducer of claim 7 wherein said one or more supporting anchors comprise a copper tab.

9. The displacement transducer of claim 7, wherein said surface is a biological surface.

10. A method of measuring a displacement of a biological structure, wherein said method comprises:
mounting a fiber optic cable directly onto said biological structure, wherein said fiber optic cable is potted in epoxy resin and substantially encased in a tube formed from a shape memory alloy, and wherein said fiber optic cable is etched with a series of regularly spaced lines directing a laser light source with a wavelength matching a line spacing of one of the regularly spaced line into one end of the fiber optic cable to provide a preferential reflection; and measuring fiber deformation as a function of change in the light wavelength from the preferential reflection.

11. The method of claim 10, wherein said biological structure is a biological surface.

* * * * *